United States Patent [19]

Smith

[11] 4,165,439
[45] Aug. 21, 1979

[54] PROCESS FOR THE SELECTIVE ORTHO-ALKYLATION OF A PHENOL IN THE PRESENCE OF A COPPER-CHROMIUM CATALYST

[75] Inventor: William E. Smith, Schenectady, N.Y.

[73] Assignee: General Electric Company, Pittsfield, Mass.

[21] Appl. No.: 853,315

[22] Filed: Nov. 21, 1977

Related U.S. Application Data

[63] Continuation of Ser. No. 676,503, Apr. 13, 1976, abandoned.

[51] Int. Cl.² .................... C07C 37/12; C07C 39/06
[52] U.S. Cl. ................................................ 568/804
[58] Field of Search ............. 260/621 R, 624 C, 620, 260/619 R; 568/804

[56] References Cited

U.S. PATENT DOCUMENTS

| | | | |
|---|---|---|---|
| 3,446,856 | 5/1969 | Hamilton, Jr. | 260/620 |
| 3,716,589 | 2/1973 | Kotanigawa et al. | 260/621 R |
| 3,718,704 | 2/1973 | Chapman et al. | 260/671 M |

*Primary Examiner*—Werren B. Lone
*Attorney, Agent, or Firm*—Morgan, Finnegan, Pine, Foley & Lee

[57] ABSTRACT

A process for the selective ortho-alkylation of a phenolic compound which comprises reacting at a temperature of at least 185° C. in the presence of a copper chromite catalyst said phenolic compound with an alkanol of 1 to about 12 carbon atoms.

8 Claims, No Drawings

PROCESS FOR THE SELECTIVE ORTHO-ALKYLATION OF A PHENOL IN THE PRESENCE OF A COPPER-CHROMIUM CATALYST

This is a continuation, of application Ser. No. 676,503 filed Apr. 13, 1976 now abandoned.

BACKGROUND OF THE INVENTION

It is well known in the art to alkylate phenols having at least one unsubstituted ortho position. Many prior art processes have been disclosed as being non-selective and indiscriminate in regard to the nature of the products that are formed. Winkler et al, U.S. Pat. No. 2,448,942, for example, discloses a process for the preparation of penta-substituted phenols. The Winkler et al patent mentions that one may employ either alcohol or methyl ether in the vapor phase using various metal oxides such as aluminum oxide, thorium oxide, zirconium oxide, zinc oxide, iron oxide, chromium oxide, barium oxide, manganese oxide, magnesium oxide, calcium oxide, etc. as the catalyst. Alumina is the preferred catalyst. The Winkler et al process, however, is somewhat indiscriminate and lacks specificity for ortho-alkylation to the relative exclusion of alkylation in the meta- and para- positions.

Winkler et al teach that the reaction is carried out at superatmospheric pressures at temperatures in the range of 300° C. to about 450° C. However, temperature of above 430° C. have been noted, e.g., in Hamilton, U.S. Pat. No. 3,446,856, to cause a decrease in the yield of alkylated product. When phenol and methanol are reacted at temperatures above 450° C., Hamilton teaches that the production of hexamethyl benzene, a non-phenolic product, is favored. For reactions of methanol with phenol, xylenol or cresol, Hamilton stated that a temperature of about 350° to 430° C. is favored in order to obtain high yields of alkylated product, while temperatures below 350° C. increase the yield of ether by-products. Temperatures of above 450° C. and superatmospheric pressures cause decomposition of the reactant and favor the production of unwanted materials. The Hamilton process was based on the discovery that magnesium oxide was a selective ortho-alkylation catalyst that was useful at atmospheric pressure at a defined temperature range.

U.S. Pat. Nos. 3,707,569 and 3,751,488 are based respectively, on the discoveries that certain tellurium-containing compounds and molybdic acid salts are useful as selective ortho-alkylation catalysts. Further, U.S. Pat. No. 3,764,630 describes a method for selectively alkylating a phenol compound with an alkanol in the presence of water and a catalytically active compound such as molybdenum oxide and alkali metal, alkaline earth metal, lead, bismuth and ammonium salts of molybdic acid in admixture with magnesium oxide. Also, U.S. Pat. No. 3,843,606 discloses a catalyst which is porous magnesium oxide powder bonded with an inert organic cellulosic polymeric binder for use in selective alkylation of phenols. Lastly, U.S. Pat. No. 3,873,628 discloses mixtures of magnesium oxide and manganese sulfate as useful catalysts for ortho-alkylation of phenols. These patents are incorporated herein by reference.

Ortho-alkylated phenols have valuable properties. They are particularly useful as the starting material for the manufacture of polyarylene ethers such as polyphenylene oxide, a valuable thermoplastic resin disclosed and claimed, for example, in A. S. Hay's U.S. Pat. No. 3,306,875.

DESCRIPTION OF THE INVENTION

It has now been discovered that a copper-chromium composition may be used as a relatively low temperature alkylation catalyst that provides high selectivity with respect to substitution in the ortho position in the reaction of phenols and alkanols. The high selectivity and the relatively mild conditions of this process make it a promising approach toward solving the problems of unsatisfactory alcohol utilization and short catalyst life associated with prior art methods.

According to this invention, there is provided a selective process for the ortho-alkylation of a phenolic compound of the general formula:

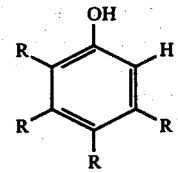

wherein each R is a monovalent substituent selected from the group consisting of hydrogen, alkyl of 1 to 12 carbon atoms, aryl of 6 to 12 carbon atoms and alkaryl of 7 to 12 carbon atoms, the process comprising reacting said phenolic compound with a lower alkanol in the presence of a copper-chromium catalyst. Examples of these substituents include methyl, ethyl, n-propyl, phenyl, o-methylphenyl, p-methylphenyl, 2,6-xylyl, and the like. Especially useful starting materials are phenol, o-cresol, m-cresol, p-cresol, o-phenylphenol and 3,5-xylenol. The preferred embodiment of the process is carried out using phenol, ortho cresol, or a mixture of the two as the phenolic starting material.

Suitable alkanols may be represented by the formula:

wherein $R_1$ is a saturated alkyl of up to about 12 carbon atoms, straight chain or branched chain. Illustrative alkanols are those wherein $R_1$ is methyl, ethyl, n-propyl, i-propyl, n-butyl, hexyl, octyl, 2-ethylhexyl, decyl, dodecyl. Preferred alkanols are lower primary and secondary alkanols, i.e., those in which $R_1$ contains from 1 to 6 carbon atoms such as methyl, ethyl, propyl, isopropyl, butyl, isobutyl, amyl and hexyl alcohols. Methanol is the preferred alkanol.

In order to obtain the maximum yield of ortho-alkylated products, it is preferred to use at least 0.5 mole of alkanol, and preferably from 1 to 3 moles of alkanol for each ortho position hydrogen in the phenolic compound to be alkylated. For example, if phenol is to be methylated to produce a maximum yield of 2,6-xylenol (2,6-dimethylphenol), it is preferred to use at least 2 moles and especially preferred to use from 2 to 6 moles of methanol for each mole of phenol. Of course, if the phenolic compound is already mono-substituted in one of the ortho-positions, maximum yields will be obtained with at least one mole of alkanol, e.g., methanol, per mole of phenolic compound, e.g., orthocresol.

The catalysts of the instant invention are copper-chromium oxide compositions, either as amorphous mixed oxides, or as crystalline copper chromite substances such as those described in H. Charcosset et al, Compt. Rend: 254, 2990-2 (1962), or as mixtures of the amorphous and crystalline substances. The copper-chromium catalysts of the instant invention can be varied in composition from about 0.05 parts to about 10 parts of copper per part of chromium. In a preferred embodiment, the copper-chromium oxide compositions are promoted by the presence of a component selected from the oxides and hydroxides of the Group I, II or III metals, manganese, iron and mixtures thereof. These promoters can constitute from about 3 to about 95% of the catalyst composition.

The catalysts of the instant invention may be prepared by a number of different methods, such as those described in U.S. Pat. No. 3,899,446, for example, which is incorporated herein by reference. An Example in this Patent describes the preparation of a copper-chromium-zinc mixed oxide composition, which after reduction is effective in bringing about the selective ortho methylation of phenol and ortho cresol by methanol at substantially lower temperatures than in the cases of the prior art catalysts. Alternatively, standard copper chromite or copper chromite precursor compositions can be promoted by impregnation with suitable metal oxides, hydroxides, carbonates, formates and the like and heating in place. In another method, copper and chromium oxides can be coprecipitated with such other promoters as zinc oxide, barium oxide, manganese oxide, cadmium oxide, magnesium oxide and the like.

In another variation, the catalyst of the instant invention can be composed of mixed pellet types. For example, a bed of copper chromite pellets mixed with magnesium oxide or zinc oxide pellets can be employed.

The catalyst is preferably used in the form of a bed through which the reactants are passed in the vapor phase. Preferred pressures are in the range from about atmospheric to about 5 atmospheres.

The instant process is carried out at a temperature of at least 185° C. The optimum alkylation temperature is in the range of from 185° C. to about 350° C.

The instant process may be carried out using a variety of reactors with varying flow rates of the reactants, varying vapor space velocities of the reactants and length of the catalyst bed. Tubular reactors, such as a glass or a metal tube filled with a bed of the catalyst may be employed. The reactor is heated with conventional means either by surrounding the reactor with an electrical heater, a heated gas, or a fused salt bath, liquid metal, etc., which can be conveniently maintained at reaction temperature by the use of immersion type electrical heaters. Alternatively, a fluid bed reactor may be used. The alkylation reaction is exothermic and, therefore, the heat of reaction can be utilized to maintain the catalyst bed at the proper reaction temperature.

The techniques are conventional and reference is made to the above-mentioned patents.

In carrying out an alkylation in accordance with the invention, any one or a mixture of phenols having an ortho hydrogen together with an alkanol may be vaporized and passed through a reactor heated to a temperature of at least 185° C. containing the copper-chromium catalyst of the invention. The alkanol can be mixed with the phenol to form a solution which is then vaporized or separate streams of the two reactants may be fed to the same or separate vaporizers and then to said reactor. Also, the reactants may be passed through the catalyst bed with a hydrogen carrier gas, for example.

The vapors issuing from the reactor are condensed in the usual fashion and the products separated in the usual fashion, for example, by crystallization, distillation, etc.

DESCRIPTION OF THE PREFERRED EMBODIMENT

The following examples are set forth to illustrate more clearly the principle and practice of this invention to those skilled in the art. Unless otherwise specified, where parts or percents are mentioned, they are parts or percents by weight.

EXAMPLE I

This example is presented to demonstrate the limited utility in orthomethylation of phenols of a copper chromite catalyst in which no alkylating component has been incorporated.

A vertical hot tube reactor (16 mm ID×70 cm effective length) was constructed from heavy wall glass, with 24/40 male and female joints. Vigreaux points were indented just above the male joint to support catalyst pellets. Thermocouple leads are fastened into three other Vigreaux indentations at points along the length. Three 4 ft.×1 in. Briskheat glass insulating heating tapes were wound onto the tube, covered with glass wool and glass tape, and connected to separate variable transformers. The tube exit was connected by a gooseneck (also heated) to an efficient condenser and collection vessel. A three-necked flask served as the evaporator, with the reactants added through a side neck by a syringe pump.

The reactor was charged with 193 grams (130 ml.) of copper chromite catalyst (Girdler G-13 3/16×3/16 in. tablets composed of 40% Cu, 25.5% Cr and the remainder oxide oxygen). The bed was activated by heating under a hydrogen-nitrogen stream, with care taken to control the exotherm (maximum temperature 300° C.).

The reactor temperature was maintained at 250° C. while a methanol-phenol mixture (5:1 molar ratio) was passed into the evaporator at 36 ml/hr. (LHSV=0.28) with a 130 ml/min. hydrogen carrier. The condensed effluent contained some methylation products—analysis by gas-liquid partition chromatography (glpc) showed the presence of o-cresol (about 5% conversion) along with small amounts (about 1% conversion) of anisole and p-cresol, and a trace of 2,6-xylenol. Gas evolution by decomposition of the methanol was substantial.

On raising the reactor temperature to 275°, 300° and 325° C., the phenol conversion increased to levels of about 10%, 20% and 25%, respectively. The selectivity to o-cresol and 2,6-xylenol remained relatively poor. At 325° C. particularly the methanol decomposition was nearly complete.

EXAMPLE II

This example is presented to demonstrate the effect of using an alkylating co-catalyst in conjunction with the copper chromite in the methylation process.

The reactor described in Example I was charged with mixed equal volumes (70 ml. each) of the copper chromite (Girdler G-13) and magnesium oxide (Harshaw Mg 0601, ⅛ in. tablets). After activation of the bed the 5:1 methanol-phenol and hydrogen carrier were passed through as in Example I, initially at 250° C. Analysis of the effluent showed that an efficient conversion to o-cresol and 2,6-xylenol had been effected. The phenolic composition (mole percentages) of the condensate on steady state operation at several temperatures is summarized in Table 1.

Table 1.

Methylation of Phenol Using Copper Chromite and Magnesia Co-Catalysts

| T. °C. | Phenol, % | o-Cresol, % | 2,6-Xylenol, % | Mesitol, % |
|---|---|---|---|---|
| 250 | 60.7 | 30.4 | 8.9 | — |
| 300 | 40.3 | 34.9 | 24.6 | 0.2 |
| 325 | 31.1 | 37.3 | 31.1 | 0.5 |

EXAMPLE III

The reactor and catalyst bed described in Example II was operated with a liquid feed composed of methanol and o-cresol in 2:1 ratio passed into the evaporator at 36 ml/hr. The phenolic product composition of the condensate on steady state operation at several temperatures is summarized in Table 2.

Table 2.

Methylation of o-Cresol Using Copper Chromite and Magnesia Co-Catalysts

Phenolic Composition

| T. °C. | o-Cresol, % | 2,6-Xylenol, % | Mesitol, % |
|---|---|---|---|
| 250 | 78.0 | 22.0 | — |
| 300 | 58.1 | 41.4 | 0.5 |
| 325 | 51.4 | 47.1 | 1.5 |

EXAMPLE IV

This example is presented to demonstrate the effect of incorporating an alkylating component into the copper chromite catalyst in the methylation process.

The Girdler G-13 copper chromite was impregnated with 10% by weight of zinc formate, using an aqueous solution of the formate and a rotary evaporating technique. The reactor described in Example I was charged with 130 ml. of the impregnated catalyst. Activation under hydrogen at 250° produced a catalyst containing zinc oxide (about 5% by weight relative to the initial copper chromite, produced by decomposition of the zinc formate).

With the operating temperature maintained at 250° C., the 5:1 methanol-phenol was passed in at 36 ml/hr. with the 130 ml/min. hydrogen carrier. A steady state was reached after about six hours, at which time the phenolic composition of the condensed effluent was 38.7% phenol, 37.3% o-cresol, 23.9% 2,6-xylenol and 0.1% mesitol. The efficiency remained at essentially the same level over 200 hours of operation.

EXAMPLE V

The catalyst bed described in Example IV was maintained at 270° C. while a mixture of methanol, phenol and o-cresol in 4.0:0.6:0.4. molar proportions (and 3% by weight) was passed through with the hydrogen carrier gas at 72 ml/hr. (LHSV=0.55). Analysis of the steady state effluent under these conditions indicated a phenolic composition of 30.7% phenol, 45.9% o-cresol and 23.4% 2,6-xylenol. Analysis of the uncondensed effluent revealed the presence of carbon dioxide and carbon monoxide in 1.7:1 ratio, a trace of methane, and the hydrogen present as the carrier and as a methanol decomposition product.

EXAMPLES VI–IX

Metal hydroxide-promoted (about 5% by weight) copper chromite catalysts were prepared by impregnating the copper chromite tablets with the corresponding metal formates (magnesium formate, sodium formate, calcium formate and lithium formate) and pyrolyzing the catalysts in place (maximum temperature 300° C.) during activation under hydrogen. The catalyst bed in each case was then maintained at 250° C. while the 5:1 methanol-phenol mixture was passed in at 36 ml/hr. along with the hydrogen carrier gas. The phenolic composition in the effluent was determined by glpc analysis at the one-hour point with each catalyst. The results are summarized in Table 3. In each case the catalyst activity gradually decreased, reaching relatively low levels within 24 hours of operation.

Table 3

Methylation of Phenol Using Metal Hydroxide Impregnated Copper Chromite Catalysts

| | | Phenol Composition | | | |
|---|---|---|---|---|---|
| Example | Impregnant | Phenol, % | o-Cresol, % | 2,6-Xylenol, % | Mesitol, % |
| 5 | Mg(OH)$_2$ | 58.7 | 29.8 | 11.5 | — |
| 6 | NaOH | 54.5 | 34.6 | 10.9 | — |
| 7 | Ca(OH)$_2$ | 22.8 | 32.2 | 43.2 | 1.8 |
| 8 | LiOH | 5.0 | 9.6 | 66 | 19.4 |

EXAMPLE X

The 5:1 methanol-phenol feed was passed into the reactor charged with 130 ml. of Harshaw barium oxide "stabilized" copper chromite Cu 1107 (⅛ in. tablets containing 33% CuO, 38% Cr$_2$O$_3$ and 9% BaO) as in the above examples, with the bed temperature maintained at 250° C. The phenolic composition of the effluent at a steady state was 69.8% phenol, 26.5% o-cresol and 3.7% 2,6-xylenol. Small amounts of anisoles and ring hydrogenated products (about 3% total) were also detected.

EXAMPLE XI

A catalyst was prepared by impregnating copper chromite (Girdler G-13, see Example I) with 10% by weight of aluminum isopropoxide, using an isopropanol solution of the impregnant and a rotary evaporation technique. The dried catalyst was activated with hydrogen in place as in the above examples, then was converted to an "alumina"-modified form by treatment with a 5:1 methanol-phenol feed containing 5% of water by weight, passed in at 36 ml/hr. with the hydrogen carrier gas, the operating temperature being maintained at 250°. The phenolic composition of the steady state efluent was 53.5% phenol, 34.6% o-cresol, and 11.9% 2,6-xylenol.

EXAMPLE XII

The reactor described in Example I was charged with 216 grams (130 ml.) of a catalyst composed of 52% Zn, 5.7% Cu, 13% Cr and the remainder oxide oxygen (Girdler T-359, pieces averaging about 3/16×3/16 in.).

After activation under hydrogen, the bed was maintained at 280° C. while the 5:1 methanol-phenol feed was passed in at 36ml/hr. The steady state phenolic composition in the effluent was 60.6% phenol, 34.4% o-cresol and 5.0% 2,6-xylenol.

EXAMPLE XIII

The 5:1 methanol-phenol feed was passed into a bed of 206 grams (130 ml.) of catalyst containing, before activation, 16% Cu, 32% Cr and 25% Cd as the oxides (Girdler T 988, 3/16×3/16 in. pellets). The methylation process was slow at 250° C.; about 2% o-cresol was formed at the LHSV of 0.28. At 325° the phenolic composition in the effluent was 49.2% phenol, 32.7% o-cresol and 18.1% 2,6-xylenol.

EXAMPLE XIV

The reactor described in Example I was charged with 130 ml. of Girdler G-89 catalyst having a nominal composition of 38% Cu, 31% Cr and 3% Mn as oxides. After activation, the 5:1 methanol-phenol mixture was passed in at 36 ml/hr. with hydrogen as in the above examples. The results with steady state operation at several temperatures are summarized in Table 4.

Table 4

| | Methylation of Phenol Using Cu—Cr—Mn Catalyst | | | |
|---|---|---|---|---|
| | | Phenolic Composition | | |
| T, °C. | Phenol, % | o-Cresol, % | 2,6-Xylenol, % | Mesitol, % |
| 250 | 63.3 | 31.1 | 5.6 | — |
| 275 | 35.5 | 42.5 | 22.0 | — |
| 300 | 26.0 | 44.0 | 29.7 | 0.3 |
| 325 | 15.0 | 42.9 | 40.8 | 1.2 |

The phenolic products were accompanied by small amounts (about 3% total) of anisoles and ring hydrogenation products. No undecomposed methanol was detected in the effluent at 325° C.

EXAMPLE XV

A barium oxide-stabilized copper chromite catalyst (3/16 in. tablets composed of 34.0% Cu, 30.7% Cr and 5.7% Ba as oxides) was impregnated with 10% by weight of zinc formate and pyrolyzed in place as in Example IV. A mixture of ethanol and phenol (5:1 molar ratio, containing 4% water) was passed through a 130 ml. bed of the activated catalyst maintained at 250° at 36 ml/hr. with the usual hydrogen carrier gas. The steady state effluent contained, according to glpc analysis, acetaldehyde (minor), ethanol, water, and the phenolic derivatives phenol (62.0%), 2-ethylphenol (29.8%) and 2,6-diethylphenol (8.2%) (molar percentages). Very small amounts (1% or less) of 4-ethylphenol, 2,4-diethylphenol and 2,4,6-triethylphenol were also detected and characterized.

EXAMPLE XVI

The catalyst bed described in Example XV was maintained at 300° while a 3:1 molar mixture of allyl alcohol and phenol (and 4.5% water) was passed into the evaporator at 36 ml/hr. Analysis of the effluent indicated a phenolic composition of 72.4% phenol, 24.6% 2-n-propylphenol and 3.0% 2,6-di-n-propylphenol. No allylphenol or other unsaturated derivatives were detected.

EXAMPLE XVII

A catalyst was prepared by grinding the copper-chromite composition described in Example XV, blending the resultant powder with an equal weight of zinc oxide powder, and tableting the blend using 5% by weight of Dow Methogel HG65. The pellets were calcined at 800° F. then activated with hydrogen and used with a 3:1 n-propanol-phenol feed at 300° C. and LHSV=0.3. The phenolic composition at a steady state was 52.4% phenol, 30.1% 2-n-propylphenol, 15.5% 2,6-di-n-propylphenol and a total of about 2% of p-substituted products.

Obviously, other modifications and variations of the present invention are possible in the light of the above teachings. It is therefore to be understood that changes may be made in the particular embodiments of the invention described which are within the full intended scope of the invention as defined by the appended claims.

What is claimed is:

1. A process for the selective ortho-alkylation of a phenolic compound of the general formula:

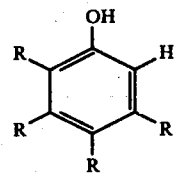

wherein each R is a monovalent substituent selected from the group consisting of hydrogen, alkyl of 1 to 12 carbon atoms, aryl of 6 to 12 carbon atoms and alkaryl of 7 to 12 carbon atoms, the process comprising reacting at a temperature of at least 185° C. in the presence of copper chromite catalyst said phenolic compound with an alkanol of 1 to about 12 carbon atoms.

2. A process as defined in claim 1 wherein each R is hydrogen.

3. A process as defined in claim 1 wherein the alkanol is methanol.

4. The process as defined in claim 1 wherein the copper-chromite catalyst is admixed with a promoter selected from the oxides and hydroxides of Group I, II or III metals, manganese, iron or mixtures thereof.

5. The process as defined in claim 4 wherein the catalyst is in the form of copper chromite pellets admixed with pellets of oxides of the Group I, II or III metals, manganese and iron, and mixtures thereof.

6. The process as defined in claim 4 wherein the promoter is zinc oxide.

7. The process as defined in claim 1 wherein the alkylation is carried out at a temperature of from 185° C. to about 350° C.

8. A process for the selective ortho-alkylation of a phenolic compound of the general formula:

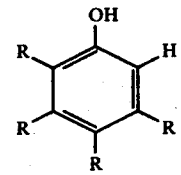

wherein each R is a monovalent substituent selected from the group consisting of hydrogen, alkyl of 1 to 12 carbon atoms, aryl of 6 to 12 carbon atoms and alkaryl of 7 to 12 carbon atoms, the process comprising reacting at a temperature of from 185° C. to about 350° C. in the presence of copper chromite catalyst said phenolic compound with an alkanol of 1 to about 12 carbon atoms.

* * * * *

UNITED STATES PATENT AND TRADEMARK OFFICE
CERTIFICATE OF CORRECTION

PATENT NO. : 4,165,439

DATED : August 21, 1979

INVENTOR(S) : William Edward Smith

It is certified that error appears in the above-identified patent and that said Letters Patent are hereby corrected as shown below:

Col. 1, before "BACKGROUND OF THE INVENTION", insert --This invention is directed to a process for selectively ortho alkylating a phenolic compound which comprises reacting the phenolic compound with an alkanol in the presence of a copper-chromium catalyst.--

, line 30, "temperature" should be --temperatures--

Col. 4, line 22, "are" should be --were--

Col. 5, line 47, "evaporating" should be --evaporation--.

Signed and Sealed this

First Day of January 1980

[SEAL]

Attest:

SIDNEY A. DIAMOND

*Attesting Officer*     *Commissioner of Patents and Trademarks*